United States Patent [19]

Fujiwake

[11] Patent Number: 5,756,297
[45] Date of Patent: May 26, 1998

[54] METHODS AND APPARATUS FOR ANALYZING NUCLEIC ACID MOLECULES

[75] Inventor: Hideshi Fujiwake, Kyoto, Japan

[73] Assignee: Shimadzu Corporation, Kyoto, Japan

[21] Appl. No.: 691,205

[22] Filed: Aug. 1, 1996

[30] Foreign Application Priority Data

Aug. 31, 1995 [JP] Japan ................. 7-223836

[51] Int. Cl.$^6$ .................. C12Q 1/68; C12Q 1/70; C12P 19/34; G01N 33/00
[52] U.S. Cl. .................. 435/6; 435/5; 435/91.1; 435/291; 435/29; 435/34; 435/287.1; 435/288.2; 436/94
[58] Field of Search .................. 435/6, 5, 91.2, 435/91.1, 7.1–7.9, 291, 29, 34, 287.1, 288.2–288.9; 436/94

[56] References Cited

U.S. PATENT DOCUMENTS 4,500,641  2/1985  Van Den Engh .

OTHER PUBLICATIONS

Haussmann et al. Z. Naturforsch Sect C. Biosci 46: 433–442, 1991.

*Primary Examiner*—W. Gary Jones
*Assistant Examiner*—Dianne Rees
*Attorney, Agent, or Firm*—Keiichi Nishimura

[57] ABSTRACT

A sample containing nucleic acid molecules is mixed with a same volume of reagent such as isopropanol to render the nucleic acid molecules insoluble. This solution containing the nucleic acid molecules in insoluble condition is introduced into a flow cell and exposed therein to light from a light source. Scattered light from the nucleic acid molecules is detected by light sensors and analyzed by a computer.

6 Claims, 1 Drawing Sheet

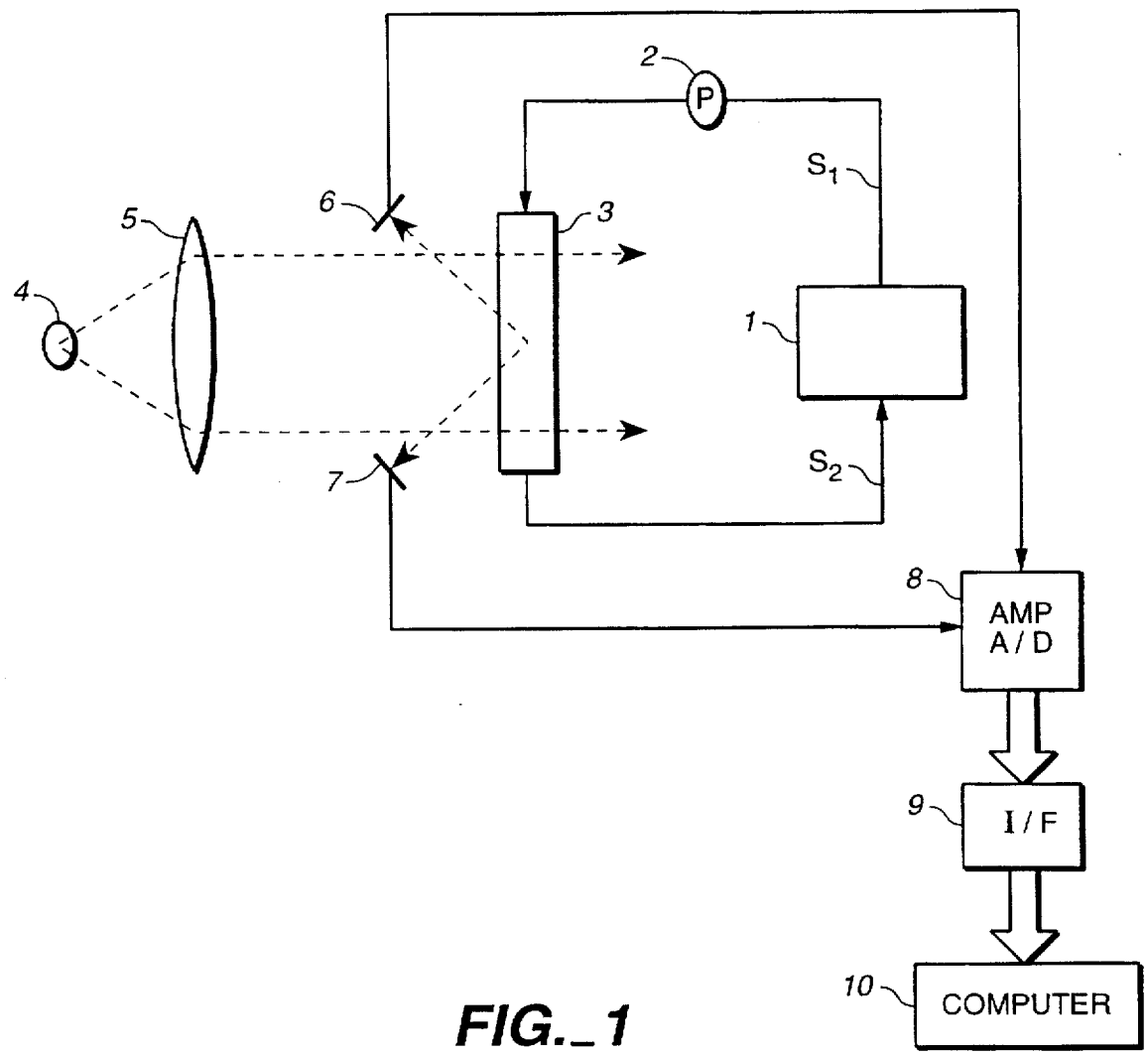
FIG._1

METHODS AND APPARATUS FOR ANALYZING NUCLEIC ACID MOLECULES

BACKGROUND OF THE INVENTION

This invention relates to methods and apparatus for analyzing nucleic acid molecules which can be utilized in all fields of application where base sequence is to be determined or the size of nucleic acid molecules is of interest.

Nucleic acids are high polymer compounds containing nitrogen, found in cells in the state of being combined with protein. DNA, in particular, serves as a memory for heredity data and a template for protein synthesis inside cells, and properties of DNA such as its molecular size have been studied. Prior art methods of such studies have been by electrophoresis by first preparing a migration plate (or a gel plate). When polyacrylamid gel is used for this purpose, for example, the migration plate may be prepared by placing polyacrylamid gel, a small amount of a cross linking agent and a catalyst between a pair of glass plates for polymerization. A nucleic acid solution is thereafter applied to the migration plate, and a high voltage is applied to the migration plate by providing an electrode tank. In response to the application of such a high voltage, the nucleic acid begins to migrate at a different speed according to the molecular weight. Thus, the molecular weight can be detected, for example, by dying the migration map.

Besides methods by electrophoresis, methods by ultra-centrifugal separation and quantitative analysis have been carried out in the case of nucleic acids with very large molecules (with molecular weight greater than 600,000 ), and methods by liquid chromatography have been used in the case of very small nucleic acid molecules (with molecular weight smaller than 30,000).

Of these prior art methods, those by electro-phoresis are not capable of quickly determining the size of nucleic acid molecules because time-consuming processes are involved such as preparation of a migration plate, electrophoresis and dying. Methods with an ultra-centrifuge are feasible only for the separation of very large molecules, and methods by a liquid chromatograph are feasible only for the separation of very small molecules.

SUMMARY OF THE INVENTION

It is therefore an object of this invention to provide new methods and apparatus for analyzing nucleic acid molecules such as their sizes.

According to this invention, nucleic acid molecules and their sizes are analyzed spectroscopically by a scattering method. Apparatus according to this invention, with which the above and other objects can be accomplished, may be characterized as comprising a reactor part where nucleic acid molecules are rendered insoluble, a liquid-transporting pump for transporting the insoluble nucleic acid molecules in the reactor part to a sample cell, a light source serving to expose the insoluble nucleic acid molecules transported to the sample cell to light, and a detection part where scattered light from the sample cell is detected.

BRIEF DESCRIPTION OF THE DRAWINGS

The unique drawing, or FIG. 1, accompanying this application, which serves to explain the principles of the invention together with the description, is a schematic block diagram of an apparatus embodying this invention.

DETAILED DESCRIPTION OF THE INVENTION

As explained briefly above, the method according to this invention is characterized by the step of analyzing properties of nucleic acid molecules spectroscopically by using scattered light. More in detail, after nucleic acid molecules are rendered insoluble in a solution, they are exposed to light and the scattered light is analyzed. Throughout herein, nucleic acid molecules will include both DNA and RNA, and examples of DNA will include those derived from all kinds of samples collected from an live system (such as tissues, blood, marrow liquid, saliva, milk, urine and feces from an animal source and roots, stems, leaves, flowers and fruits from a vegetable/plant source), as well as viruses, bacteria and cells contained in environmental samples (such as soils and water) and foods such as meat, milk and eggs.

Nucleic acid molecules in a sample are rendered insoluble by mixing the sample, for example, with a reagent such as isopropanol, polyethylene glycol and ethanol. Examples of such a reagent for making nucleic acid molecules insoluble are not limited by these cited above but may also include any that can cause nucleic acid molecules to precipitate. Such a reagent may be directly added to a sample of the kind described above but, if there is a large amount of impurities, it is preferable to preliminarily remove such impurities in the sample, separating and refining the DNA. Separation and refinement of DNA are generally carried out by extraction by using phenol•chloroform after the sample is treated with an enzyme or a surfactant. The size of the precipitate depends generally on the size of the nucleic acid molecule rendered insoluble. If the reagent is sufficiently dilute, it may be only the nucleic acid molecules that precipitate, and it may be concluded that the size of the nucleic acid molecule is proportional to that of such a precipitate. In other words, the size of nucleic acid molecules can be determined by measuring the size of the precipitates. The diameter of insoluble nucleic acid molecules is in the range of 50–200nm.

Scattered light is measured by placing the nucleic acid molecules rendered insoluble inside a sample cell and exposing them to light. Sample cells of both a stationary cell type and a flow cell type may be used, but a flow cell type is preferred in the case of a continuous measurement. Any light source in the ultraviolet and visible range such as semiconductor lasers, gas lasers, mercury lamps and tungsten lamps can be used as the light source. Examples of detection system includes a group of photoelectric tubes of silicon photo-cells arranged at selected positions (such as backward and sideward positions) and a detector system with a plurality of detection elements arranged in a ring formation. Scattered light may be detected in all directions, not merely at sideward and backward positions. When scattered light in all directions is to be detected, an integrating sphere may be set around the sample cell to collect the entire scattered light.

FIG. 1 shows schematically an apparatus embodying this invention as comprising a reactor part 1 and a flow cell 3. The reactor part 1 may comprise a funnel-shaped container with an open top, serving to receive therein a sample solution containing nucleic acid molecules and a solution for rendering the nucleic acid molecules insoluble and to thereby cause the nucleic acid molecules to precipitate. Alternatively, the nucleic acid molecules may be rendered insoluble in a separate container and the solution containing the nucleic acid molecules already rendered insoluble may be placed inside the reactor part 1. The nucleic acid molecules may be rendered insoluble, for example, by adding and mixing the same volume of isopropanol as the sample solution. The mixing may be effected by inserting a stirrer rod into the container and causing it to rotate by means of a motor or by using a magnetic stirrer.

A liquid delivery pipe S1 is inserted into the reactor part 1 and attached to the inlet of the flow cell 3 for delivering nucleic acid molecules. A collector pipe S2 has one end thereof connected to the outlet of the flow cell 3 for collecting nucleic acid molecules and the other end thereof inserted into the reaction part 1 such that the insoluble nucleic acid molecules can circulate between the reactor part 1 and the flow cell 3. A liquid circulating pump (P) 2 is provided for effecting this circulation.

The flow cell 3 is made of a transparent material such as glass or quartz, a light source 4 being placed near one of its side surfaces. The light source 4 may comprise, for example, a semiconductor laser, and the emitted light therefrom is focused by a collector lens 5 to irradiate the flow cell 3. Light sensors 6 and 7 for detecting scattered light respectively in a sideward direction and in a backward direction are disposed at specified positions with respect to the light source 4 and the flow cell 3. (This positional relationship is not accurately reflected in FIG. 1). Outputs from the light sensors 6 and 7 are received through an amplifier analog-to-digital converter (AMP A/D) 8 and an interface (I/F) by a computer 10 which is adapted to compute the size of the nucleic acid molecules on the basis of data received from the light sensors 6 and 7.

With the apparatus structured as shown in FIG. 1, the same volumes of isopropanol and a liquid sample are mixed together for rendering nucleic acid molecules insoluble. Next, the solution is placed inside the reactor part 1, and the liquid circulating pump 2 is activated. The solution is thereby introduced into the flow cell 3 and exposed therein to light from the light source 4. Scattered light is detected by the sensors 6 and 7 at different scattering angles.

The intensity of scattered light detected by each of the light sensors 6 and 7 is proportional to the product of the intensity of the incident beam and the cross-sectional area of scattering, the latter being proportional to the square of the diameter of the molecule. Thus, it is possible to estimate the diameter of the nucleic acid molecule from the intensity of the scattered light if the intensity of the incident light is constant. In other words, standard samples containing molecules with known sizes (or diameters) may be used to preliminarily establish a relationship between the molecular diameter and the light intensity to be detected, and a comparison graph thus prepared may be consulted to calculate the diameter of the nucleic acid molecules in the sample. This calculation is carried out by the computer 10.

If two or more insoluble nucleic acid molecules are present in the path of the incident light, the total intensity of scattered light is the sum of contributions from all these molecules. Thus, use is generally made of a sufficiently diluted sample solution. Measurements of light intensity are taken successively as the liquid is circulated into the flow cell 3, and a histogram of the intensity or the calculated sizes of the molecules is prepared in a known manner.

In summary, the present invention makes it possible to analyze the size of nucleic acid molecules quickly, unlike by the prior art method by electrophoresis which is both time and labor consuming and unlike the ultra centrifugal method which imposes a severe limitation on the size of the molecules to be analyzed.

What is claimed is:

1. A method of analyzing nucleic acid molecules, said method comprising the steps of:

rendering insoluble nucleic acid molecules which are in a soluble condition in a solution and thereby causing said nucleic acid molecules to precipitate in said solution;

exposing to light said precipitated nucleic acid molecules rendered insoluble in said solution; and measuring the size of said precipitated nucleic acid molecules from light scattered by said precipitated insoluble nucleic acid molecules.

2. The method of claim 1 further comprising the step of diluting said solution sufficiently such that light scattered by only one of said nucleic acid molecules can be measured.

3. The method of claim 1 further comprising the steps of causing said light to be scattered by a standard sample containing molecules with a known diameter and measuring and recording the intensity of light scattered thereby.

4. The method of claim 1 further comprising the step of causing said solution to circulate while said nucleic acid molecules are being exposed to light and while said scattered light is being measured.

5. A method of analyzing nucleic acid molecules, said method comprising the steps of:

adding a reagent selected from the group consisting of isopropanol, polyethylene glycol and ethanol to a sample containing soluble nucleic acid molecules in a solution and thereby causing said nucleic acid molecules to become insoluble and precipitate in said solution;

exposing to light said precipitated nucleic acid molecules in said solution; and measuring the size of said precipitated nucleic acid molecules by causing light to be scattered by said insoluble nucleic acid molecules.

6. The method of claim 5 wherein said solution, which contains said nucleic acid molecules rendered insoluble, is caused to flow through a flow cell on which said light is made incident.

* * * * *